(12) United States Patent
Ujagare et al.

(10) Patent No.: US 8,193,354 B2
(45) Date of Patent: Jun. 5, 2012

(54) PROCESS FOR PREPARATION OF GEMCITABINE HYDROCHLORIDE

(75) Inventors: Ashish Ujagare, Mumbai (IN); Dattatrey Kochrekar, Mumbai (IN); Matthew Uzagare, Mumbai (IN)

(73) Assignee: Arch Pharmalabs Limited, Mumbai (IN)

( * ) Notice: Subject to any disclaimer, the term of this patent is extended or adjusted under 35 U.S.C. 154(b) by 839 days.

(21) Appl. No.: 11/914,890

(22) PCT Filed: Apr. 25, 2006

(86) PCT No.: PCT/IN2006/000144
§ 371 (c)(1),
(2), (4) Date: Nov. 19, 2007

(87) PCT Pub. No.: WO2007/049294
PCT Pub. Date: May 3, 2007

(65) Prior Publication Data
US 2008/0167463 A1    Jul. 10, 2008

(30) Foreign Application Priority Data
Oct. 28, 2005    (IN) .......................... 1362/MUM/2005

(51) Int. Cl.
*C07D 403/04* (2006.01)
*C07D 407/04* (2006.01)
(52) U.S. Cl. ...................................... 544/317; 536/28.5
(58) Field of Classification Search ................. 544/317; 536/28.5
See application file for complete search history.

(56) References Cited

U.S. PATENT DOCUMENTS

| 4,526,988 A | 7/1985 | Hertel |
| 4,808,614 A | 2/1989 | Hertel |
| 5,637,688 A | 6/1997 | Berglund |

FOREIGN PATENT DOCUMENTS

| EP | 0 630 905 A1 | 12/1994 |
| EP | 0 712 860 A2 | 5/1996 |
| WO | WO 2005/095430 A1 | 3/2004 |

OTHER PUBLICATIONS

International Search Report for PCT/IN2006/000144 filed Apr. 25, 2006.

*Primary Examiner* — Venkataraman Balasubramanian
(74) *Attorney, Agent, or Firm* — Merchant & Gould P.C.

(57) ABSTRACT

A process for isolating β-anomer enriched Gemcitabine hydrochloride by converting Gemcitabine base into Gemcitabine hydrochloride followed by its purification using solvents from the series of water soluble ethers like 1,4-dioxane or Monoglyme.

25 Claims, No Drawings

PROCESS FOR PREPARATION OF GEMCITABINE HYDROCHLORIDE

FIELD OF INVENTION

The present invention relates to a novel process for the preparation of Gemcitabine hydrochloride of the formula (I). More particularly the present invention relates to the isolation and purification of Gemcitabine hydrochloride of formula (I)

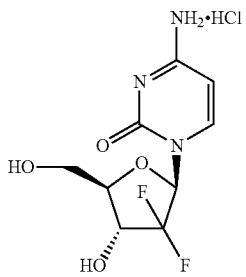

Formula (I)

BACKGROUND OF THE INVENTION

The chemical species, 1-(2'-Deoxy-2',2'-difluoro-D-ribofuranosyl)-4-aminopyrimidin-2-one of Formula (II) is generically known as Gemcitabine.

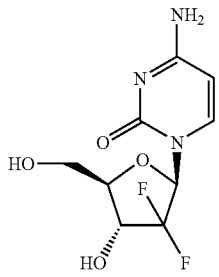

Formula (II)

Gemcitabine of formula (II) a pyrimidine analog, is structurally similar to cytarabine, but has a wider spectrum of antitumour activity due to its different cellular pharmacology and mechanism of action. Gemcitabine belongs to the group of medicines called antimetabolites. Gemcitabine is a type of chemotherapy for treating many types of cancers including lung, pancreatic cancers. It can interfere with the growth of rapidly growing cells like cancer cells and causes cell death.

Isolation and crystallization of Gemcitabine hydrochloride disclosed in U.S. Pat. Nos. 4,526,988 and 4,808,614, adopts laborious chromatographic purifications in different stages which make the process industrially nonviable.

The process disclosed in U.S. Pat. No. 5,637,688 for the isolation and crystallization of Gemcitabine hydrochloride comprises following steps:
a) Deblocking of β-1-(2'-deoxy-2',2'-difluoro-3',5'-di-O-benzoyl-D-ribofuranosyl)-4-aminopyrimidin-2-one with a catalytic amount of an alkylamine in the presence of methanol or ethanol in an environment essentially free of water;
b) Treating the resulting solution with hydrochloric acid and an antisolvent selected from the series of acetone, acetonitrile, tetrahydrofuran, propanol, butanol, isobutanol, sec-butanol and isopropanol;
c) Purifying the resulting Gemcitabine hydrochloride.

In EP0630905, isolation involves dissolution of Gemcitabine hydrochloride (1:1) in hot water and then precipitated by acetone to get 80% β-anomer rich product which is further purified by re-dissolving in hot water and then again precipitated by acetone to get 99% β-anomer of Gemcitabine hydrochloride.

It also describes isolation of Gemcitabine base of 99% purity from Gemcitabine or its addition salt by dissolving in hot water and increasing pH to 7-9 isolating Gemcitabine of 99% and is further converted into Gemcitabine hydrochloride.

WO2005/095430 discloses the isolation of Gemcitabine hydrochloride whereby crude 2'-deoxy-2',2'-difluorocytidine base is dissolved in isopropanol and then precipitated by hydrochloric acid and filtered off. The solution so obtained is then further purified by water and acetone as solvent system which is already reported in prior art. The process of purification disclosed in WO2005/095430 includes dissolving Gemcitabine HCl in water to increase the purity and then again dissolving in water and acetone for further purification thereby increasing the unit operation.

Therefore there is a long felt need of a process for the isolation and purification of Gemcitabine hydrochloride, which is selective for the beta-anomer of the Gemcitabine hydrochloride giving high yield and purity.

Also there is a need of a process of purification which does not require any reversion of hydrochloride to base by adding other bases like alkyl amine and again converting back to hydrochloride salt which increases unit operation without giving appreciable yields or a process of purification which does not require any pH adjustment as disclosed in prior art.

OBJECTS OF THE INVENTION

Therefore it is an object of the present invention to provide a process for the selective isolation of beta-anomer of Gemcitabine hydrochloride.

It is further object of the present invention to provide a process for purification of Gemcitabine hydrochloride.

Another object of the present invention is to provide a process for isolation & purification, which employs the use of water miscible ethers like 1,4-dioxane or Monoglyme.

Yet another object of the present invention is to provide a process for beta-anomer of Gemcitabine hydrochloride in high yield along with high purity (99.9%).

SUMMARY OF THE INVENTION

Thus according to an aspect of the present invention there is provided a process for the isolation of β-anomer enriched Gemcitabine hydrochloride of Formula (I) comprising conversion of Gemcitabine base having α and β anomers into β-Gemcitabine hydrochloride using organic solvent chosen from the series of water miscible ethers like 1,4-dioxane or Monoglyme.

According to another aspect of the present invention there is also provided a process for the purification of β-Gemcitabine hydrochloride of Formula (I) comprising dissolving of Gemcitabine hydrochloride (β-anomer enriched) in water and selectively crystallizing using organic solvent chosen from water miscible ethers like 1,4-dioxane or Monoglyme.

DETAILED DESCRIPTION

The preparation and isolation of Gemcitabine hydrochloride from the mixture of α and β anomers of Gemcitabine base involves the use of novel solvents such as water miscible ethers like 1,4-dioxane or Monoglyme. The ratio of isolated Gemcitabine hydrochloride is in the range 80-90% β and 4-12% α anomer.

The process for the purification of Gemcitabine hydrochloride containing 80-90% β-anomer further uses the concept of solvent and antisolvent wherein water is used as solvent and antisolvent is chosen from the series of water soluble ethers resulting into selective crystallization of Gemcitabine hydrochloride with high isomeric purity and higher yields and further purification to yield product of 99.9% The solvents for the purification of Gemcitabine hydrochloride selected are rich in β-anomer (80-90%) to give purity of 99.9% with improved yield.

Entire Schematic Representation for the Isolation and Purification of Gemcitabine Hydrochloride is Shown as Follows:

1) Reduction of 2-deoxy-2,2-difluoro-D-erythro-pentafuranos-1-ulose-3,5-dibenzoate 2-deoxy-2,2-difluoro-pentafuranos-1-ulose-3,5-dibenzoate was reduced to benzoylated lactol (2-Deoxy-2,2-difluoro-D-ribofuranose-3,5-dibenzoate) using Vitride which is sodium bis(2-methoxyethoxy) aluminium hydride and commercially available as a 70% w/w solution in toluene as reducing agent and Tetrahydrofuran as solvent in temperature range of −40 to −70° C. The duration of the reaction was around 30-120 minutes. 2-deoxy-2,2-difluoro-pentafuranos-1-ulose-3,5-dibenzoate was isolated by usual method resulting in the yield in the range of 90-95% and having purity of 80-85%.

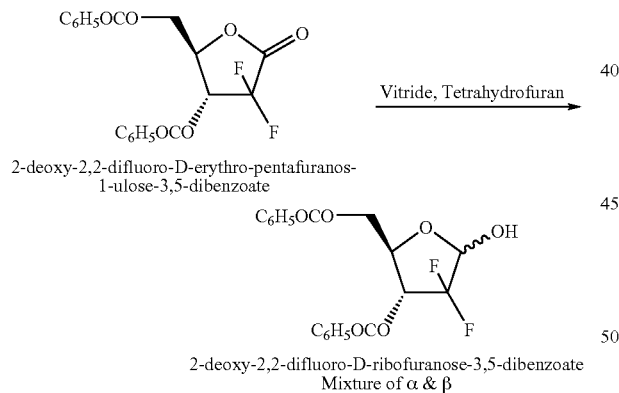

2) Methyl sulfonation of 2-deoxy-2,2-difluoro-D-ribofuranose-3,5-dibenzoate

Benzoylated lactol (2-Deoxy-2,2-difluoro-D-ribofuranose-3,5-dibenzoate) so obtained was subjected to reaction with methanesulfonyl chloride in methylene dichloride as solvent at temperature of −25 to +10° C., preferably at −20 to 5° C., more preferably at −20 to 0° C. to form 2-deoxy-2,2-difluoro-D-ribofuranose-3,5-dibenzoate-1-methane sulfonate 90-95 yield & HPLC purity 80-85%.

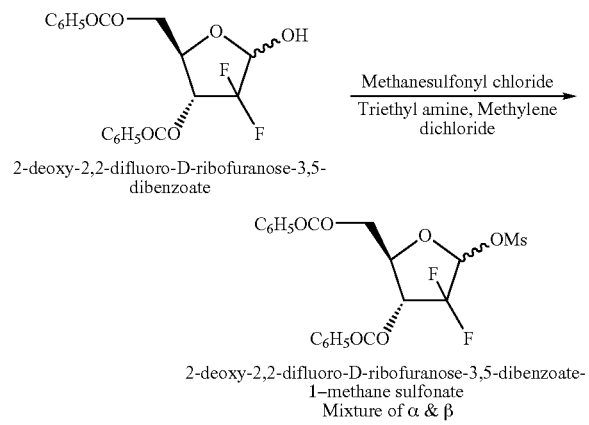

3) Condensation of 2-deoxy-2,2-difluoro-D-ribofuranose-3,5-dibenzoate-1-methanesulfonate with N-acetyl bis trimethylsilyl cytosine derivative followed by preparation of Gemcitabine base The bistrimethylsilyl derivative of acetyl cytosine was prepared by treatment of acetyl cytosine with hexamethyldisilazane and trimethylsilyl chloride in ethylenedichloride. The product from step 2 was then subjected to coupling with bistrimethylsilyl derivative of acetyl cytosine in presence of trimethylsilyl triflate at 80-82° C., resulting into 2'-deoxy-2',2'-difluoro-N-1-acetyl cytidine-3',5'-dibenzoate (1.2-1.3 w/w).

The 2'-deoxy-2',2'-difluoro-N-1-acetyl cytidine-3',5'-dibenzoate was hydrolysed in methanol 1:8 to 15 w/v using ammonia at a temperature in the range of −10 to +10° C. preferably at −5 to +5° C. for 5-20 hours preferably 8-10 hours. After the hydrolysis, the methanolic solution was concentrated to get a thick mass which was then dissolved in water and extracted with ethyl acetate followed with diisopropyl ether. Aqueous layer so obtained was concentrated under vacuum at 30-60° C. preferably at 40-45° C. resulting into Gemcitabine base.

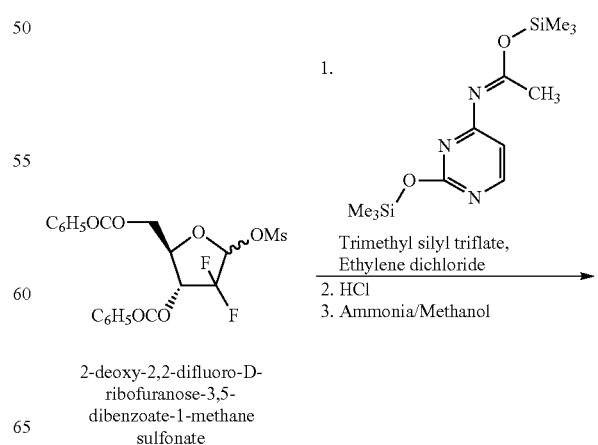

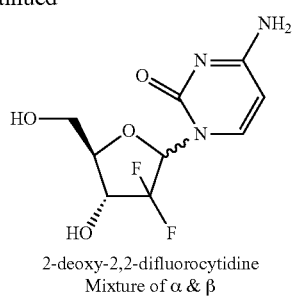

2-deoxy-2,2-difluorocytidine
Mixture of α & β

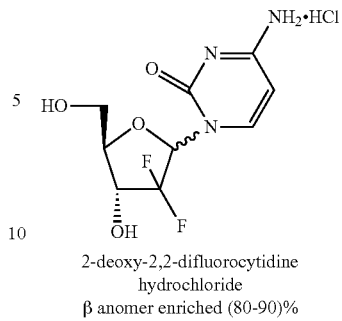

2-deoxy-2,2-difluorocytidine
hydrochloride
β anomer enriched (80-90)%

Isolation of Gemcitabine Hydrochloride:

The Gemcitabine base so obtained was converted into its hydrochloride by adding solvents like 1,4-dioxane or Monoglyme in ratio of 1:4-12 (w/v) preferably 1:5-8 (w/v) and heating the contents at 40-90° C. preferably at 50-70° C. more preferably at 60-68° C. followed by cooling the contents to 10-30° C. preferably 10-15° C. to give crude (solid) Gemcitabine hydrochloride having 80-90% of β-anomer & 4-12% of α-anomer.

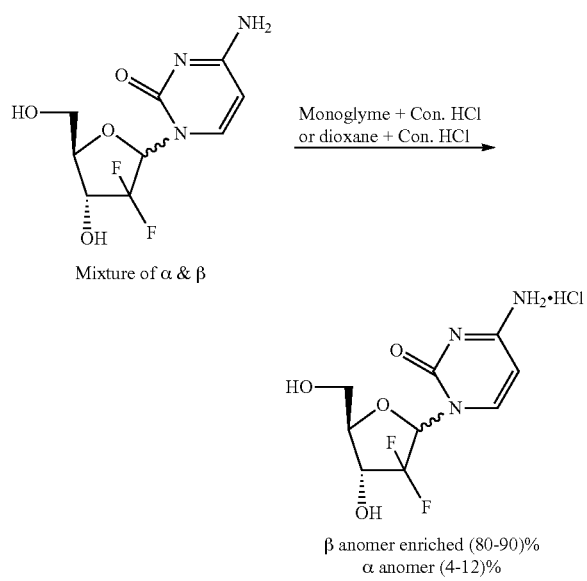

Mixture of α & β

β anomer enriched (80-90)%
α anomer (4-12)%

β anomer
99.9%

Purification of Gemcitabine Hydrochloride:

The isolated product obtained in the above reaction has α-anomer (4-12%) and β-anomer (80-90%) which is further purified to 99.9% by dissolving crude Gemcitabine hydrochloride in water 1:4-8 (w/v) preferably 1:5-7 (w/v) and heating the contents at 40-90° C. preferably at 50-70° C. more preferably 60-68° C. to get a solution to which solvents like 1,4-dioxane or Monoglyme in the ratio of 1:40-100 (w/v) preferably 1:50-70 (w/v) are added followed by heating the contents at 40-90° C. preferably at 50-70° C. followed by cooling to 10-30° C. preferably 10-15° C. to get Gemcitabine hydrochloride of purity 99.9%. The overall yield at this stage with respect 2'-deoxy-2',2'-difluoro-N-1-acetyl cytidine-3',5'-dibenzoate is 15 to 16%.

The preferred solvent is water and the preferred anti solvent is selected from the series of water soluble ethers preferably 1,4-dioxane and Monoglyme with improved yield and high purity of 99.9%. The most preferred solvents for the isolation of β-anomer of Gemcitabine hydrochloride and purification of Gemcitabine hydrochloride rich in β-anomer are the water miscible ethers like 1,4-dioxane or Monoglyme.

The purity & assay of the product thus obtained is analyzed using HPLC method for the details of which USP is to be referred.

Column specification: 4.6 mm×25 cm column, that contains 5 µL packing L7.

Wave length selected: 275 nm

Mobile phase: Prepare a filtered and degassed solution containing 13.8 g of monobasic sodium phosphate and 2.5 ml of phosphoric acid in 1000 ml of water.

Flow rate: 1.2 ml/min

Diluant: Filtered and degassed water for HPLC

The details of the invention, its objects and advantages are explained hereunder in greater details in relation to non-limiting exemplary illustrations. The examples are merely illustrative and do not limit the teaching of this invention and it would be obvious that various modifications or changes in the procedural steps by those skilled in the art without departing from the scope of the invention and shall be consequently encompassed within the ambit and spirit of this approach and scope thereof.

EXAMPLES

Example 1

Preparation of 2-deoxy-D-erythro-2,2-difluoro-ribofuranose-3,5-dibenzoate 2-deoxy-D-erythro-2,2-difluoro-pentafuranos-1-ulose-3,5-dibenzoate (200 g) was dissolved in (2 L) of tetrahydrofuran in a 5 L round bottom flask. (0.2 L) of vitride (70% solution in toluene) was added between −50 to −70° C. The reaction was continued for 60 minutes. On completion, reaction was arrested by adding methanol (0.24 L) followed by hydrolysis with 7% HCl (1.3 L). After stirring for ~30 min the aqueous layer was separated at RT. The aqueous layer was repeatedly extracted with Ethyl acetate (0.8 L×2). The collected organic layer was washed with brine (0.5 L×2) and 5% aqueous NaHCO$_3$ (0.5 L×2) followed by brine (0.5 L×2). The organic layer was concentrated under vacuum to get thick oil (0.2 kg).

Example 2

Preparation of 2-deoxy-D-erythro-2,2-difluoro-ribofuranose-3,5-dibenzoate-1-methanesulfonate 2-deoxy-D-erythro-2,2-difluoro-ribofuranose-3,5-dibenzoate (0.2 kg) oil was dissolved in (2 L) Methylenedichloride. The reaction mixture was cooled to 0 to −20° C. and (0.12 L) triethylamine was added. To this stirred mixture was added (0.06 L) Methane sulfonylchloride drop wise between −20° C. to −15° C. The reaction was stirred at same temperature till completion of reaction (in ~3 hours). Temperature was brought to room temperature & 5% HCl (0.9 L) was added to reaction. The aqueous layer was separated and extracted with Methylene dichloride (0.4 L×2). The organic layer was washed with brine (0.5 L×2) & by 5% aqueous sodium bicarbonate followed by brine (0.5 L×2). The organic layer was collected and concentrated to give oil (0.24 kg).

Example 3

Preparation of Gemcitabine Base

Acetyl cytosine (200 g) was added to 1,2-dichloroethane (4 L) in 10 L round bottom flask. Hexamethyldisilazane (0.34 L) was added to the slurry. The resulting mixture was heated to distill out ~1 L mixture. The reaction mass cooled to 50° C. under nitrogen and trimethyl silyl chloride (0.015 L) was added to the mixture. The resulting mixture was refluxed at 82-85° C. for 3 hours. The solution was cooled to 45° C. under nitrogen and distilled at 45-50° C. to obtain solid. Fresh ethylene dichloride (2.6 L) was added to the solid so obtained followed by addition of Trimethyl silyl triflate (0.26 L). To this solution of mesylate (0.24 L) obtained from example no 2 dissolved in ethylene dichloride (1.2 L) was added. The resulting mixture was heated to reflux at 86-92° C. for 18 hours till 2-deoxy-2,2-difluoro-ribofuranose-3,5-dibenzoate-1-methnesulfonate was consumed. The reaction mixture was cooled at room temperature and 5% HCl (1.8 L) was added to the reaction mixture followed by separation of aqueous layer and extraction with ethylene dichloride (0.4 L×2). The combined organic layer was washed with brine (1 L×2). The collected organic layer was treated with sodium bicarbonate (0.2 Kg) to neutralize acidity. The dried organic layer was concentrated to give oil (0.26 kg). The resulting oil obtained in previous example (0.26 kg) was dissolved in methanol (3.4 L). The resulting solution was cooled to −5 to +5° C. and ammonia gas purged through the mixture under stirring for 8-10 hours between −5 to +5° C. till complete consumption of 2',2'-difluoro-2'-deoxy-N-acetyl cytidine-3',5'-dibenzoate. The temperature was allowed to increase to room temperature. The solution was concentrated under vacuum to obtain oil which was dissolved in water (0.8 L). Ethyl acetate (0.2 L) was added to it and the mixture was stirred for 15 min. The aqueous layer separated was extracted with ethyl acetate (0.2 L). The combined ethyl acetate layer was extracted with (2.6 L) water. The aqueous layer was filtered and concentrated under vacuum at 40-45° C. to give oil (0.1 Kg) with HPLC (for α and β) for Gemcitabine base.

Example 4A

Isolation of Gemcitabine Hydrochloride

To the 20 g of thick oil of Gemcitabine base obtained as in example 3 was added 1,4-Dioxane (120 ml) and the mixture was heated to 60°-68° C. and stirred for 15 minutes. Conc. HCl (10 ml) was then added to the mixture and the contents were heated at same temperature for one hour. Reaction mass was then cooled to 10-15° C. and maintained for 30 minutes. The solid thus obtained was filtered off and washed with 1,4-Dioxane and dried under vacuum at 55-60° C. to get 8 g material with Specific Optical Rotation i.e.[α]$_D$=+40° and HPLC purity of 85% β-anomer and 8% α-anomer.

Example 4B

Purification of Gemcitabine Hydrochloride 10 g material obtained using protocol of example 4A was taken in water (60 ml) and the mixture was heated to 55-60° C. to get a clear solution. 1,4-Dioxane (600 ml) was added to the solution under stirring and continued for one hour at 60-68° C. The contents were cooled to 10-15° C. & the mixture was stirred at this temperature for 30 min and filtered, washed with 1,4-Dioxane and dried at 55-60° C. under vacuum to get 7.5 g compound of HPLC purity 99.9% β-anomer with Specific Optical Rotation i.e.[α]$_D$=+47°.

Example 5A

Isolation of Gemcitabine Hydrochloride

To the 20 g of thick oil of Gemcitabine base as obtained in example 3 was added Monoglyme (120 ml) and the mixture was heated at 60-68°C. and stirred for 15 minutes. Conc. HCl (10 ml) was then added to the mixture and the contents were heated at same temperature for one hour. Reaction mass was then cooled to 10-15° C. and maintained for 30 minutes. The solid thus obtained is filtered off and washed with Monoglyme and dried under vacuum at 55-60° C. to get 8 g material having HPLC purity with 85% β-anomer & 9% α-anomer, Specific Optical Rotation i.e.[α]$_D$=+40°

Example 5B

Purification of Gemcitabine Hydrochloride 10 g material obtained as in example 5A was taken in water (60 ml) and the mixture was heated to 60-65° C. to get a clear solution. Monoglyme (600 ml) was added to the solution under stirring and continued for one hour at 60-65° C. The contents were cooled to 10-15° C. The mixture was stirred at this temperature for 30 minutes and filtered, washed with Monoglyme and dried at 55-60° C. under vacuum to get 7.3 g product with HPLC purity 99.9% β-anomer with Specific Optical Rotation i.e.[α]$_D$=+47°.

The invention claimed is:

1. A process of isolating β-anomer enriched Gemcitabine hydrochloride from the mixture of α & β anomers of Gemcitabine base, the method comprising:
   a) adding water soluble ether to Gemcitabine base
   b) heating the mixture to dissolve the base (oil) and adding thereto hydrochloric acid;

c) cooling the mixture;
d) isolating the precipitated β-anomer enriched Gemcitabine hydrochloride; and
e) purifying the β-anomer enriched Gemcitabine hydrochloride by employing the water soluble ether.

2. The process according to claim 1, wherein the precipitated β-anomer enriched Gemcitabine hydrochloride comprises 80-90% β-anomer and 4-12% α-anomer.

3. The process according to claim 1, wherein the purified α-anomer enriched Gemcitabine hydrochloride comprises 99.9% β-anomer.

4. The process according to claim 3 wherein the ratio of Gemcitabine base to said water soluble ether is in the range of 1:5-8(w/v).

5. The process according to claim 1 wherein the Gemcitabine base along with the water soluble ether is heated at a temperature of 40-90° C.

6. The process according to claim 5 wherein the Gemcitabine base along with the water soluble ether is heated at a temperature of 50-70° C.

7. The process according to claim 5 wherein the Gemcitabine base along with the water soluble ether is heated at a temperature of 60-68° C.

8. The process according to claim 1 wherein the reaction mixture is cooled to a temperature of 10-30° C.

9. The process according to claim 8 wherein the mixture is cooled to a temperature of 10-15° C.

10. The process according to claim 1, wherein the water soluble ether comprises 1,4-dioxane or Monoglyme.

11. A process for purification of β-anomer enriched Gemcitabine hydrochloride comprising:
a) providing β-anomer enriched Gemcitabine hydrochloride that was isolated from a mixture of α & β anomers of Gemcitabine in a process employing a water soluble ether;
b) dissolving the β-anomer enriched Gemcitabine hydrochloride in water by heating the contents;
c) adding the water soluble ether and cooling the mixture; and
d) crystallizing the purified β-anomer enriched Gemcitabine hydrochloride to provide purified β-anomer enriched Gemcitabine hydrochloride.

12. The process according to claim 11 wherein the ratio of Gemcitabine hydrochloride to water is in the range of 1:4-8 (w/v)

13. The process according to claim 12 wherein the ratio of Gemcitabine hydrochloride to water is in the range of 1:5-7 (w/v).

14. The process according to claim 11 wherein the Gemcitabine hydrochloride and water are heated at a temperature of 40-90° C.

15. The process according to claim 14 wherein the Gemcitabine hydrochloride and water are heated at a temperature of 50-70° C.

16. The process according to claim 14 wherein the Gemcitabine hydrochloride and water are heated at a temperature of 60-68° C.

17. The process according to claim 11 wherein the ratio of solution of Gemcitabine hydrochloride to said water soluble ether in the range of 1:40 -100(w/v)

18. The process according to claim 17 wherein the ratio of solution of Gemcitabine hydrochloride to said water soluble ether is in the range of 1:50-70(w/v)

19. The process according to claim 11 wherein the said water soluble ether is selected from the group consisting of 1,4-dioxane and Monoglyme.

20. The process according to claim 11 wherein the reaction mixture is cooled to a temperature of 10-30° C.

21. The process according to claim 20 wherein the reaction mixture is cooled to a temperature of 10-15° C.

22. The process according to claim 11 wherein the process yields β-anomer enriched Gemcitabine hydrochloride comprises 99.9% β-anomer.

23. The process according to claim 11, further comprising:
providing β-anomer enriched Gemcitabine hydrochloride from a reaction that included 2'-deoxy-2',2'-difluoro-N-acetyl cytidine-3',5'-dibenzoate;
wherein the process yields purified β-Gemcitabine hydrochloride with yield of 15-16% with respect to the 2'-deoxy-2',2'-difluoro-N-acetyl cytidine-3',5'-dibenzoate.

24. A process of purifying β-anomer enriched Gemcitabine hydrochloride, the process comprising:
providing a mixture of α & β anomers of Gemcitabine base;
adding water soluble ether to Gemcitabine base
heating the mixture comprising water soluble ether and Gemcitabine base to dissolve the base (oil);
adding hydrochloric acid to the heating or heated mixture;
cooling the mixture comprising hydrochloric acid;
isolating the precipitated β-anomer enriched Gemcitabine hydrochloride.
dissolving the isolated β-anomer enriched Gemcitabine hydrochloride in water by heating;
adding the water soluble ether to the heated water comprising β-anomer enriched Gemcitabine hydrochloride and then cooling; and
crystallizing the purified β-anomer enriched Gemcitabine hydrochloride to provide purified β-anomer enriched Gemcitabine hydrochloride.

25. The process according to claim 1, wherein the ratio of Gemcitabine base to water soluble ether is in the range of 1:4-12(w/v).

* * * * *